United States Patent [19]

Kervinen

[11] Patent Number: 5,341,678

[45] Date of Patent: Aug. 30, 1994

[54] METHOD FOR DETERMINING THICKNESS OF FERROMAGNETIC MATERIAL DEPOSITION ON NUCLEAR FUEL RODS

[75] Inventor: John A. Kervinen, Palo Alto, Calif.

[73] Assignee: General Electric Company, San Jose, Calif.

[21] Appl. No.: 58,152

[22] Filed: May 12, 1993

[51] Int. Cl.$^5$ .............................................. G01B 21/08
[52] U.S. Cl. .................................. 73/150 R; 376/255
[58] Field of Search ............... 376/245, 258, 305, 252, 376/253, 255; 324/225, 441, 700, 229, 239; 73/150 R

[56] References Cited

U.S. PATENT DOCUMENTS

| | | | |
|---|---|---|---|
| 3,737,764 | 6/1973 | Dufayet | 324/40 |
| 4,088,946 | 5/1978 | Charles et al. | 324/220 |
| 4,303,885 | 12/1981 | Davis et al. | 324/237 |
| 4,673,877 | 6/1987 | Sakamoto et al. | 324/225 |
| 4,700,134 | 10/1987 | Scharton et al. | 324/220 |
| 4,853,638 | 8/1989 | Endou et al. | 324/441 |
| 4,901,017 | 2/1990 | Zinke | 324/239 |
| 4,991,301 | 2/1991 | Hore | 33/366 |
| 5,124,641 | 6/1992 | Netter et al. | 324/230 |

OTHER PUBLICATIONS

Eddy Current Evaluation of Nuclear Control Rod by C. V. Dodd. Material Evaluation (USA) May 1974, vol. 32, No. 5 pp. (93–99).

Primary Examiner—Donald P. Walsh
Assistant Examiner—Meena Chelliah
Attorney, Agent, or Firm—J. S. Beulick

[57] ABSTRACT

A method for determining the thickness of ferromagnetic material deposited on a nuclear fuel rod. Calibration samples of known thickness and known permeability are placed between the probe of an eddy current sensor and a conductive surface. A plurality of calibration points are plotted to provide a characteristic complex impedance diagram for a probe excited at a predetermined frequency. Then the complex impedance of the probe excited at the selected frequency is measured when in proximity to a fuel rod having a corrosion layer of unknown thickness and unknown magnetic permeability. For each probe position, the two components of the complex impedance, i.e., the inductive reactance and the resistance, are determined and plotted on the characteristic complex impedance diagram. The position of the measured data point relative to the calibration points enables one to determine the lift-off error due to the presence of ferromagnetic material.

15 Claims, 2 Drawing Sheets

1

METHOD FOR DETERMINING THICKNESS OF FERROMAGNETIC MATERIAL DEPOSITION ON NUCLEAR FUEL RODS

FIELD OF THE INVENTION

This invention generally relates to electromagnetic test methods for evaluating the integrity and corrosion resistance of nuclear fuel rod cladding. In particular, the invention relates to techniques for improving the accuracy of the results of such electromagnetic test methods.

BACKGROUND OF THE INVENTION

Electromagnetic test methods are commonly used in evaluation of the integrity of nuclear fuel rod cladding and in the evaluation of the relative performance, such as resistance to corrosion, of cladding materials which are subjected to the reactor core operating environment. In particular, electromagnetic test methods are used to measure the thickness of a layer of corrosion formed on the outer circumferential surface of the fuel rod cladding.

The conventional test for measuring corrosion thickness on a fuel rod uses an eddy current sensor, the probe of which is placed in proximity to the fuel rod cladding, separated only by a layer of corrosion. The probe is coupled to an instrument for displaying the inductive reactance of the probe when in proximity to the fuel rod. The probe of a typical eddy current sensor has a coil of conductive wire which in effect acts as both a transmitter and a receiver of magnetic flux. When the coil is driven with an alternating current, an alternating magnetic flux emanates from the coil. This alternating magnetic flux induces alternating eddy currents in the conductive fuel rod cladding, which is typically made of Zircaloy. These alternating eddy currents in turn produce an alternating magnetic flux which induces an alternating "bucking" current which opposes the alternating drive current through the probe coil. The instrument coupled to the probe is used to measure the resulting decrease in the current flowing through the probe, which decrease is a measure of the inductive reactance of the probe.

The inductive reactance is a function of the distance separating the probe coil from the conductive sample in which the eddy currents are induced. Thus, the inductive reactance of the probe, when in contact with a layer of corrosion at a particular point along the fuel rod cladding, is a measure of corrosion thickness at that point. This separation distance between the cladding and the probe is commonly referred to as the "lift-off".

During normal operation of reactors, it is quite common for the reactor coolant to transport dissolved particles which leach out from the reactor circulation piping and which tend to deposit on the nuclear fuel rods in the form of crud. If the crud deposit contains ferromagnetic material, the presence of this ferromagnetic material will adversely affect the electromagnetic test results without the knowledge of the person conducting such tests. This is because the conventional method for measuring lift-off determines the probe inductive reactance only, not the probe resistance, i.e., the conventional method does not determine the complex impedance of the probe of the eddy current sensor.

At present there is no method for detecting the presence of ferromagnetic material in the crud deposits on the fuel rod cladding at the time when the electromagnetic tests are being conducted. This is because the instrumentation which is employed to perform the electromagnetic test has been designed to determine only the proximity of a metallic conductor to a probe and not the probe complex impedance.

SUMMARY OF THE INVENTION

The present invention improves the accuracy of conventional electromagnetic test methods for determining the thickness of corrosion formed on the outer surface of nuclear fuel rod cladding. The invention is an electromagnetic test method which allows the performer of the electromagnetic testing to detect the presence of ferromagnetic material in the corrosion layer and then quantify the effects of that ferromagnetic material on the accuracy of the test results. The test results can then be corrected by subtracting the error due to the coupling between the ferromagnetic material and the test instrument probe.

The first step in accordance with the method of the invention involves the acquisition of empirical data for a given eddy current probe operating at a predetermined excitation frequency. The probe complex impedance is measured when one of a multiplicity of calibration samples is placed between the probe and a conductive surface. Each calibration sample has a different effective permeability. A respective complex impedance is determined when the probe is in contact with each respective calibration sample. These data points map the increase in complex impedance of the probe as the effective permeability of the calibration samples increases.

The lift-off trajectory for a probe having no proximal ferromagnetic material follows a well-known path. That lift-off trajectory, however, is increasingly altered as ferromagnetic material of increasing effective permeability is introduced. Thus, alteration of the lift-off trajectory indicates the presence of ferromagnetic material. Each of those altered lift-off trajectories terminate at a common point representing the complex impedance of the probe in air.

The data points obtained for calibration samples of increasing effective permeability are useful in detecting the presence of ferromagnetic material in a corrosion layer deposited on fuel rod cladding and then quantifying the error in the lift-off measurement attributable to the permeability of that ferromagnetic material. The measured lift-off can then be normalized to eliminate the effect of proximal ferromagnetic material on the probe. A particular probe will have a characteristic complex impedance diagram for each different probe excitation frequency.

Once the characteristic complex impedance diagram has been obtained for the selected excitation frequency, the complex impedance of the probe excited at the selected frequency is measured when in proximity to a fuel rod having a corrosion layer of unknown thickness and unknown magnetic permeability. The probe complex impedance is measured at a multiplicity of positions along the outer circumferential surface of the fuel rod. The fuel rod is scanned both axially and azimuthally, at incremental axial distances and incremental azimuth angles. For each probe position, the two components of the complex impedance, i.e., the inductive reactance and the resistance, are determined and plotted on the characteristic complex impedance diagram. The position of the data point relative to the lift-off loci enables one to determine the lift-off error due to the presence of ferromagnetic material. When this lift-off error is subtracted from the raw measured lift-off, the true lift-off is obtained, which in turn provides an accurate measure of corrosion thickness on the fuel rod cladding.

DETAILED DESCRIPTION OF THE PREFERRED EMBODIMENT

The thickness of a layer of corrosion formed on the outer circumferential surface of an irradiated nuclear fuel rod is determined using an eddy-current sensor. The probe of the eddy current sensor is placed against the surface of the corrosion and an alternating drive current coupled into the probe coil produces an alternating magnetic flux that induces alternating eddy currents in the fuel rod cladding, which is made of a conductive alloy such as Zircaloy. These eddy currents in turn produce an alternating bucking current in the probe which opposes the drive current. The resulting decrease in the current across the probe coil is a measure of the distance separating the probe and the cladding, i.e., the thickness of the corrosion. This distance will hereinafter be referred to as the "lift-off distance" of the probe from the metallic surface of the fuel rod cladding.

Figure 1:
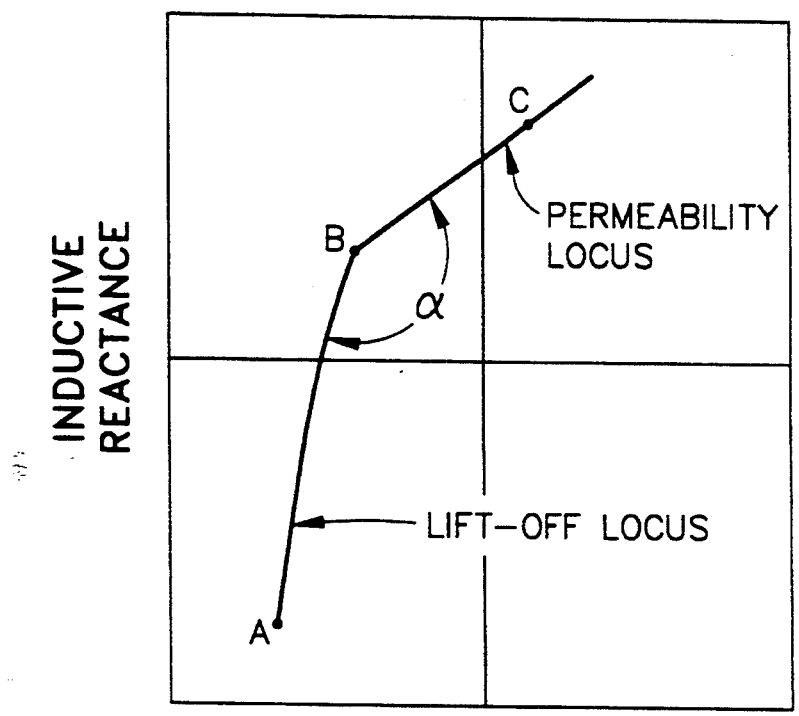
FIG. 1 is a complex impedance diagram in which the inductive reactance is plotted on the vertical axis and the resistance is plotted on the horizontal axis for a probe separated from fuel rod cladding by a variable distance.

FIG. 1 is a plot of the inductive reactance versus the resistance as measured by an eddy current sensor having a cathode ray tube. In the absence of corrosion, the probe of the eddy current sensor will be in contact with the metallic surface. The impedance of the probe when in contact with the metallic surface is indicated by point A in FIG. 1. In the presence of corrosion, the probe will be separated from the metallic surface by an amount equal to the corrosion thickness. Empirical studies have shown that as the corrosion thickness increases, the probe impedance will change by following a well-defined trajectory from point A to point B in FIG. 1. This trajectory is commonly known as the "lift-off locus". Point B is the probe impedance in air, that is, the probe has been separated from the metallic surface by a distance sufficient so that the probe is not affected by the metallic surface. Because the geometry and frequency are fixed in the present application, the impedance trajectory from point A to point B is dependent only on the electrical resistivity of the metallic surface.

If the probe of the eddy current sensor is placed in contact with ferromagnetic material, the probe's impedance at contact will be point C in FIG. 1. The location of point C relative to point B is dependent on the effective magnetic permeability of the material. A decrease or an increase in the effective magnetic permeability will cause the point C to be respectively closer to or further away from point B, following a well-defined trajectory commonly known as the "permeability locus". The angle e between the lift-off locus (trajectory A–B) and the permeability locus (trajectory C–B) shown in FIG. 1 is commonly referred to as the "relative phase angle".

Figure 2:
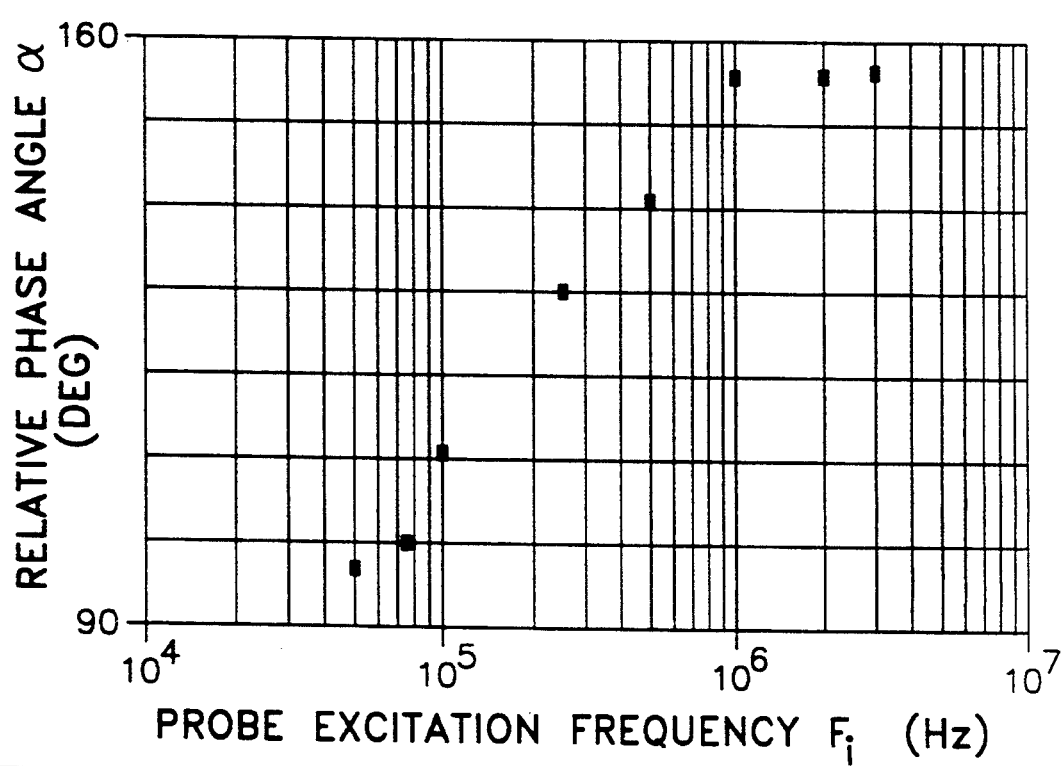
FIG. 2 is a logarithmic graph in which the relative phase angle between the lift-off locus and the permeability locus is plotted against the probe excitation frequency.

It has been determined empirically that the relative phase angle $\alpha$ is dependent on the probe excitation frequency F as shown in FIG. 2. The values for the data points plotted in FIG. 2 are listed below:

| F (Hz) | $\alpha$ (deg) |
|---|---|
| $3.0 \cdot 10^6$ | 156.25 |
| $2.0 \cdot 10^6$ | 156.19 |
| $1.0 \cdot 10^6$ | 155.78 |
| $5.0 \cdot 10^5$ | 140.83 |
| $2.5 \cdot 10^5$ | 129.28 |
| $2.0 \cdot 10^5$ | 110.6 |
| $7.5 \cdot 10^4$ | 99.8 |
| $5.0 \cdot 10^4$ | 96.6 |

As can be seen from FIG. 2, at frequencies of $10^6$ Hz or greater, which are typically employed in lift-off measurements, the relative phase angle is large, which makes the permeability locus nearly opposite to the lift-off locus. At these higher excitation frequencies, any ferromagnetic substance in proximity to the probe will thus cause an apparent lift-off to be greater than the actual lift-off, thereby introducing an error into the lift-off measurement, i.e., the thickness of a layer of ferromagnetic corrosion as measured by an eddy current probe will be greater than the actual thickness.

To detect the presence of ferromagnetic material in the corrosion layer of a nuclear fuel rod and to quantify its effect on the measurement of lift-off, the probe excitation frequency must be reduced, thereby reducing the relative phase angle, and the probe impedance trajectory must be monitored. In accordance with the method of the present invention, the probe excitation frequency is selected so that the phase angle between the lift-off locus and the permeability locus is less than a predetermined angle, e.g., less than 155°. Preferably the probe excitation frequency is selected so that the phase angle between the lift-off and permeability loci is about 110° or less.

Figure 3:
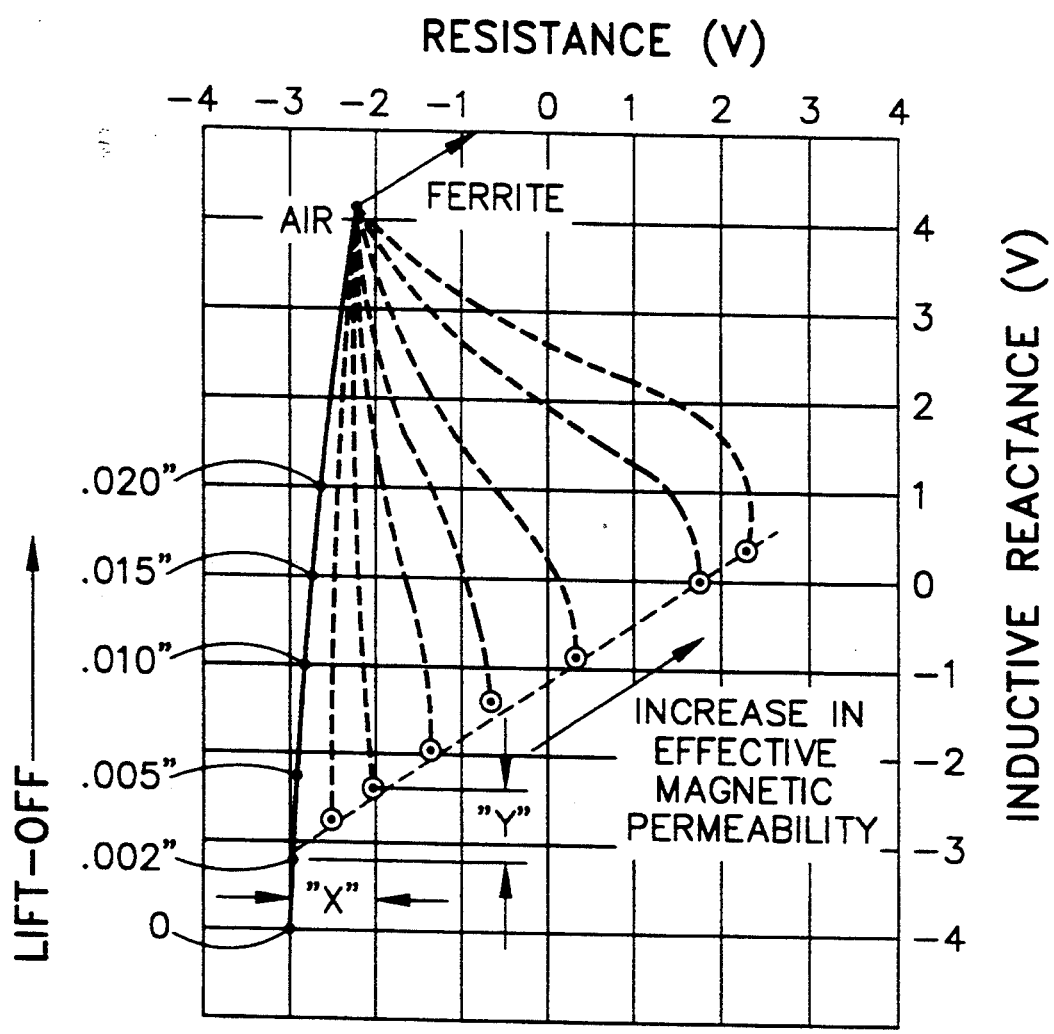
FIG. 3 is a complex impedance diagram showing the effect of increasing amounts of $MnZnFe_2O_4$ on the probe impedance for a probe excitation frequency of 100 kHz.

For example, FIG. 3 is a probe impedance diagram obtained at a probe excitation frequency of 100 kHz for a number of ferromagnetic samples inserted between the probe and the cladding. Moving from left to right, the data points correspond to ferromagnetic samples of increasing effective permeability. The dashed curves represent the lift off of the probe away from the calibration sample. The samples were fabricated from 2-mil-thick plastic shim stock coated with a variable number of layers of ferromagnetic paint. The ferromagnetic paint comprised ferrite ($MnZnFe_2O_4$) powder at a known concentration. Alternatively, other ferrite powders could be used. When the shim stock samples are coated with an increasing number of layers of ferromagnetic paint, the resulting calibration samples have ferromagnetic coatings of increasing surface density, i.e., increasing effective permeability.

As shown in FIG. 3, if there is no ferromagnetic substance present, the probe impedance trajectory, with increasing lift-off, will follow the solid curve from the point corresponding to zero corrosion to the point corresponding to a corrosion thickness which produces the probe impedance in air. In the presence of ferromagnetic material, however, the impedance trajectory will be altered as shown by the dashed curves. With increasing effective permeability, the lift-off loci shift rightward and upward. In particular, for a known thickness separating the probe from the metallic surface of the cladding, i.e., shim thickness 2 mils, the complex impedance measured by the probe for respective samples travels along a trajectory which lies parallel to the permeability locus, the error increasing as the effective permeability of the respective samples increases.

The magnitude of the deviation from the lift-off trajectory depends on the effective permeability of the ferromagnetic material deposited on the fuel rod. FIG. 3 shows that a substance with an effective permeability X will cause an apparent error in the lift-off by the amount Y. The ratio of X to Y is determined by the slope of the trajectory along which the data points for the ferrite samples are plotted. This slope is dependent on the relative phase angle $\alpha$, which is in turn a function of the probe excitation frequency F. Thus, the error Y can be decreased by decreasing the probe excitation frequency.

Applying this method of electromagnetic testing will allow the person conducting such test to know that ferromagnetic substance is present and will allow the person to quantify the effect on the test results. Once the characteristic complex impedance diagram has been obtained for the selected excitation frequency, the complex impedance of the probe excited at the selected frequency is measured when in proximity to a fuel rod having a corrosion layer of unknown thickness and unknown magnetic permeability. The probe complex impedance is measured at a multiplicity of positions along the outer circumferential surface of the fuel rod. The fuel rod is scanned both axially and azimuthally, at incremental axial distances and incremental azimuth angles. For each probe position, the two components of the complex impedance, i.e., the inductive reactance and the resistance, are determined and the data point having those coordinates is plotted on the characteristic complex impedance diagram. The position of the data point relative to the lift-off loci enables one to determine the lift-off error due to proximity of ferromagnetic material. When this lift-off error is subtracted from the raw measured lift-off datum, the true lift-off is obtained, which in turn provides an accurate measure of the thickness of the corrosion layer on the fuel rod cladding.

I claim:

1. A method for determining the thickness of a coating of substantially electrically insulating material formed on the surface of an electrically conductive component when said substantially electrically insulating material includes ferromagnetic material, said coating having an unknown thickness and an unknown permeability, comprising the steps of:
   mapping a plurality of complex impedance data points for a probe of an eddy current sensor excited with an alternating current having a predetermined frequency, each data point being acquired in the presence of ferromagnetic material having a different respective effective permeability;
   placing said probe in contact with said layer of substantially electrically insulating material of unknown thickness and unknown permeability;
   exciting said probe with an alternating current having said predetermined frequency;
   measuring the complex impedance of said excited probe in contact with said layer;
   comparing said measured complex impedance of said probe to said data points; and
   determining the portion of the inductive reactance component of said measured complex impedance which is attributable to the permeability of said layer of substantially electrically insulating material.

2. The method as defined in claim 1, wherein said step of mapping a plurality of data points comprises the steps of:
   placing said probe in proximity to an uncoated electrically conductive component, with a selected one of a multiplicity of calibration samples being installed between said probe and said uncoated electrically conductive component, each of said calibration samples being made of substantially electrically insulating material including different known amounts of ferromagnetic material;
   exciting said probe with an alternating current having said predetermined frequency; and
   plotting the complex impedance of said excited probe when said probe is in contact with an installed calibration sample, said plotting step being repeated for each calibration sample.

3. The method as defined in claim 1, further comprising the step of subtracting said portion of the inductive reactance component of said measured complex impedance which is attributable to the effective permeability of said layer of substantially electrically insulating material from the inductive reactance component of said measured complex impedance, the resulting value being used to determine the lift-off caused by said layer of substantially electrically insulating material.

4. The method as defined in claim 3, wherein said electrically conductive component is a tube made of metal or alloy.

5. The method as defined in claim 4, wherein said electrically conductive component is cladding of a nuclear fuel rod.

6. The method as defined in claim 1, wherein said predetermined frequency is less than $10^6$ Hz.

7. The method as defined in claim 1, wherein said predetermined frequency is selected so that a phase angle between a lift-off locus in the absence of ferromagnetic material and a permeability locus in the presence of ferromagnetic material is about 110 degrees or less.

8. The method as defined in claim 2, wherein each respective calibration sample comprises a strip of electrically insulating material having a different number of layers of ferromagnetic paint coated thereon.

9. A method for determining the thickness of a coating of substantially electrically insulating material formed on the surface of an electrically conductive component when said substantially electrically insulating material includes ferromagnetic material, said coating having an unknown thickness and an unknown permeability, comprising the steps of:
   placing a probe of an eddy current sensor in proximity to an uncoated electrically conductive component, with a selected one of a multiplicity of calibration samples being installed between said probe and said uncoated electrically conductive component, each of said calibration samples being made of substantially electrically insulating material including different known amounts of ferromagnetic material;

exciting said probe with an alternating current having a predetermined frequency;

calibrating the complex impedance of said excited probe when said probe is in contact with an installed calibration sample, said calibrating step being repeated for each calibration sample;

placing said probe in contact with said coated electrically conductive component;

measuring the complex impedance of said excited probe when said probe is in contact with said layer of substantially electrically insulating material of unknown thickness and unknown permeability;

comparing said measured complex impedance of said probe with said calibrated complex impedances of said probe; and determining the portion of the inductive reactance component of said measured complex impedance which is attributable to the effective permeability of said layer of substantially electrically insulating material.

10. The method as defined in claim 9, further comprising the step of subtracting said portion of the inductive reactance component of said measured complex impedance which is attributable to the effective permeability of said layer of substantially electrically insulating material from the inductive reactance component of said measured complex impedance, the resulting value being used to determine the thickness of said layer of substantially electrically insulating material.

11. The method as defined in claim 10, wherein said electrically conductive component is a tube made of metal or alloy.

12. The method as defined in claim 11, wherein said electrically conductive component is cladding of a nuclear fuel rod.

13. The method as defined in claim 9, wherein said predetermined frequency is less than $10^6$ Hz.

14. The method as defined in claim 9, wherein said predetermined frequency is selected so that a phase angle between a lift-off locus in the absence ferromagnetic material and a permeability locus in the presence of ferromagnetic material is about 110 degrees or less.

15. The method as defined in claim 9, wherein each respective calibration sample comprises a strip of electrically insulating material having a different number of layers of ferromagnetic paint coated thereon.

* * * * *